United States Patent
Haras (10) Patent No.: US 8,204,290 B2
(45) Date of Patent: Jun. 19, 2012

(54) METHOD AND DEVICE FOR PLANNING A MEDICAL IMAGING PROCEDURE

(75) Inventor: Gabriel Haras, Muecke (DE)

(73) Assignee: Siemens Aktiengesellschaft, Munich (DE)

( * ) Notice: Subject to any disclaimer, the term of this patent is extended or adjusted under 35 U.S.C. 154(b) by 606 days.

(21) Appl. No.: 12/406,207

(22) Filed: Mar. 18, 2009

(65) Prior Publication Data

US 2009/0262892 A1    Oct. 22, 2009

(30) Foreign Application Priority Data

Mar. 18, 2008    (DE) .................. 10 2008 014 737

(51) Int. Cl.
*G06K 9/00* (2006.01)
(52) U.S. Cl. ........................................ 382/131
(58) Field of Classification Search ............. 382/131
See application file for complete search history.

(56) References Cited

U.S. PATENT DOCUMENTS

| | | | | |
|---|---|---|---|---|
| 2004/0202277 A1* | 10/2004 | Okumura et al. | ............... | 378/16 |
| 2006/0193437 A1 | 8/2006 | Boeing et al. | | |
| 2009/0046833 A1* | 2/2009 | Hirokawa et al. | ............ | 378/108 |
| 2009/0141854 A1* | 6/2009 | Hirokawa et al. | ................ | 378/4 |

FOREIGN PATENT DOCUMENTS

| | | |
|---|---|---|
| DE | 102 38 894 | 3/2004 |
| EP | 1 943 951 | 7/2008 |
| WO | WO 2007/032462 | 3/2007 |

OTHER PUBLICATIONS

Dosisreduktion durch strommodulierte Dosisautomatik bei der MSCT: Vergleich von Messung and Rechnung, Lechel et al. ortschr. Röntgenstr, vol. 179 (2007).

* cited by examiner

*Primary Examiner* — Rodney Fuller
(74) *Attorney, Agent, or Firm* — Schiff Hardin LLP

(57) ABSTRACT

In a method and device for planning a medical imaging, a number of quality parameters that associate a desired image quality with the image exposure are imported into an image acquisition of an examination region that can be executed by means of an image acquisition apparatus. A number of image acquisition parameters are determined and, using the image acquisition parameters, an achievable image quality of the image exposure is concluded under consideration of an apparatus variable. The achievable image quality is compared per image region with the desired image quality and, if the achievable image quality falls short of the desired image quality, a shortfall indicator is output relative to the image region.

32 Claims, 2 Drawing Sheets

METHOD AND DEVICE FOR PLANNING A MEDICAL IMAGING PROCEDURE

BACKGROUND OF THE INVENTION

1. Field of the Invention

The present invention concerns a method for planning a medical imaging procedure as well as a corresponding device.

2. Description of the Prior Art

Methods for planning a medical imaging procedure are used, for example, for planning imaging in the framework of a radiological examination. In a radiological examination a subject (in particular a patient) is exposed with radiation. Electromagnetic beams or particle beams—for example x-rays or electrons—can be used for the exposure. As used herein, an "exposure" means a radiograph of the patient.

Due predominantly to different local material properties of the tissue structures located in the beam path, the incident radiation is affected to a different degree in the passage through the body of the patient. In particular, different tissue structures have respectively different radiation attenuation properties. The beams passing through the body of the patient thus are attenuated to different degrees. A detector signal corresponding to the intensity I of the attenuated beams can be generated by a suitable detector. Such an attenuation is frequently defined as a logarithm of the ratio of the intensity of the attenuated beams to the intensity of the primary radiation ($\sim I/I_0$). The different tissue structures can be visualized as a projection using an attenuation distribution.

In a tomography (for example x-ray computed tomography, also called CT for short) a plane of the subject (and in particular of the patient) is systematically exposed to a radiation beam from different directions The effect on the beams that are used (in particular their attenuation) is detected for each direction. Overall, a number of projections are thus acquired by means of which the attenuation distribution in the observed subject plane (and thus ultimately a spatial image exposure of said subject) is acquired.

The dose applied in such radiography of the patient with electromagnetic radiation is consistently the subject matter of intensive and critical discussions. The dose provides a measurement for the absorption of ionizing radiation (for example x-rays) by the exposed subject. In medicine, radiologically evaluated dose quantities are defined (for example in the form of an organ dose) to account for different radiation risks for various radiation types and for various tissue types.

The attempt is to keep the applied dose as low as possible proceeds according to the ALARA principle (ALARA=As Low As Reasonably Achievable).

Recently, current-modulated automatic dosing has increasingly been used, in particular in imaging by computed tomography. For example, such an automatic dosing is described in DE 102 38 894 A1 as well as in the article "Dosisreduktion durch strommodulierte Dosisautomatik bei der MSCT: Vergleich von Messung und Rechnung" ("Dose reduction via current-modulated automatic dosing in MSCT: Comparison of measurement and computation") by U. Lechel, C R Becker, G. Langenfeld-Jäger and G. Brix from Fortschritte auf dem Gebiet der Röntgenstrahlen und der bildgebenden Verfahren (Advances in the Field of X-rays and Imaging Methods), 2007 (179). An essentially constant image quality within an image exposure (in particular in the sense of a noise portion in the detector signal) is sought with such an automatic dosing. In order to achieve the constant image quality, the tube current of the computed tomography apparatus (and therefore the radiation power of its x-ray radiator) is frequently adapted to the locally different radiation attenuation relationships in the patient. The noise portion in the image exposure is normally higher the fewer radiation quanta (in particular x-ray quanta) that are registered at the detector. Stated more simply, the noise component is lower (and therefore the image quality is higher) given a high tube current than given a low tube current. Given a constant x-ray current, the noise component depends in particular on the given radiation attenuation relationships in the patient. In a first approximation, the greater the radiation attenuation property, the higher the consequent noise component in the image exposure. The applied dose in turn linearly depends on, among other things, the x-ray current-time product. Essentially, through the x-ray current modulation controlled by the image quality, as high a dose is applied as is necessary for a noise component in the detector signal that is established corresponding to the predetermined image quality.

SUMMARY OF THE INVENTION

An object of the present invention is to provide a method for planning a medical imaging procedure with which a reduction of a radiation exposure of a patient can be realized in the framework of the medical imaging. An additional object is to provide a corresponding device.

The above object is achieved according to the invention by a method wherein a number of quality parameters that associate a desired image quality with the image exposure are imported into an image acquisition of an examination region that can be executed by an image acquisition apparatus. A number of image acquisition parameters is determined, and using the image acquisition parameters an achievable image quality of the image exposure is determined dependent on an apparatus variable. The achievable image quality is compared per image region with the desired image quality, and if the achievable image quality falls below the desired image quality a shortfall indicator is output relative to the image region.

The invention proceeds from the recognition that a very high radiation attenuation property can locally result sometimes, for example given an adipose (severely overweight) patient. That has the result that the radiation penetrating the body of the patient given a radiograph can sometimes be severely attenuated locally.

The invention proceeds from the insight that the desired constant image quality cannot be achieved under the circumstances due to such a local, high radiation attenuation property, in particular given an imaging with a current-modulated automatic dosing. This can be addressed by using a device-dependent power limit for the imaging apparatus. For example: given a strong attenuation of the radiation penetrating the patient, the desired image quality can no longer be achieved (in particular in the sense of a constant noise component in the detector signal) since the apparatus current required in the framework of a current-modulated automatic dosing can sometimes, dependent on the apparatus, not be generated at the current strength required for this. Under the circumstances the achievable image quality can be far below the desired image quality.

At this point in conventional imaging systems the user (for example a physician) is informed by an appropriate means that, due to technical limitations, execution of the image exposure with the desired image quality cannot be implemented. At this point the user frequently finds himself or herself presented with the choice either adapting the desired image quality (by reducing it "haphazardly" for the entire image exposure), or to adapt one or more apparatus variables that affect the achievable image quality by changing these so the desired image quality can be achieved. For example, the scan speed of a computed tomography apparatus is an example of such an apparatus variable. It is possible to increase the achievable image quality by a reduction of the scan speed, for example. Movement artifacts can disadvantageously occur in the image acquisition given such a reduction of the scan speed. In an image acquisition that is executed using a contrast agent, such a reduction of the scan speed under the circumstances leads to the desired contrast agent distribution no longer existing in the body region to be examined. In general, the following problem can arise from such an adaptation of the image quality or of apparatus variables. If, in the cited cases (for example an image acquisition of the region of interest, the technical limitation concerns an imaging of the torso, the cited adaptation measures are not only superfluous but are possibly even unreasonable. In the one case, the image quality of the image region of interest is reduced unnecessarily, whereby a diagnostic generation is possibly made more difficult. In the other case, the patient is exposed to an unnecessary radiation exposure.

The invention recognizes the surprisingly simple possibility to circumvent the cited, sometimes patient-stressing disadvantages by indicating to a user whether the achievable image quality falling short of the desired image quality can be expected, and which image region is affected by such a shortfall.

For example, a physician can thus decide whether a reduction of the scan speed to increase the achievable image quality is reasonable and medically justifiable. In each case, a reasonably planned execution of the image acquisition is enabled by the invention, such that the patient is spared an unnecessary radiation exposure, with a simultaneous optimization of the image acquisition.

The achievable image quality of the image exposure of the examination region is concluded in advance of an execution of the image acquisition. For this purpose, a number of image acquisition parameters are determined. For example, the examination region can be the pelvis and/or the chest and/or the torso of the patient. The image acquisition parameters are values that describe the radiation attenuation property of the relevant part or parts of the patient's body. For example, a measurement system that is suitable for determining a radiation attenuation property in the patient is used for determination of the image acquisition parameters. For this purpose, the patient is radiographed with appropriate radiation, and the image acquisition parameter results from a comparison of an intensity of the radiation attenuated by the passage with the intensity of the primary radiation used. For example, the image acquisition apparatus itself can be used for such a determination of the corresponding image acquisition parameters. In principle, however, the acquisition of an image exposure is not necessary for this.

The locally different radiation attenuation relationships in the patient thus can be determined by means of the image acquisition parameters. As mentioned above, the achievable image quality namely depends in a first approximation on the given radiation attenuation relationships in the patient: the greater the local radiation attenuation property, the lower the intensity of the radiation that can be registered at the detector in comparison to the intensity of the primary radiation, and the greater the noise portion in the image exposure, and consequently the worse the achievable image quality.

Both the desired and the achievable image quality can be described by a number of quality parameters. For example, the quality parameters determine and/or describe the noise component in the image exposure, known as the image noise. In modern image acquisition apparatuses (for example in computed tomography apparatuses), the apparatus-dependent influence on the image noise is negligibly small. The image noise is normally dominated by quantum noise. Naturally the desired and/or the achievable image quality can alternatively or additionally be defined by means of other quality parameters. An example of such another quality parameter is a parameter that allows a spatial resolution and/or a contrast resolution to be determined and/or described. The capability of an imaging system to separately spatially distinguish fine details is commonly described as the spatial resolution. The contrast resolution is typically understood as the ability to make details with low contrast recognizable, a low contrast recognition capability is predominantly determined by the noise level in the image exposure. In summary it can be said that the image noise can be considered to be significant in determining the quality of the image exposure.

The image noise is among other things dependent on a current-time product. In a computed tomography apparatus the designation "tube current" is used instead of the designation of "current". Due to the given dependency of the image quality on the current-time product, it is appropriate to import a current-time product value as a quality parameter. For example, by means of the current-time product value it is also possible to quickly estimate the applied dose since the dose namely essentially linearly depends on the current-time product. The current-time product is normally specified by the unit [mAs].

As was already mentioned, the achievable image quality is dependent on the radiation attenuation property of the patient body. For this purpose, the given local radiation attenuation property is in particular described using the image acquisition parameter. For this the image acquisition parameter was in particular determined using a comparison of the intensity of the primary radiation used to the intensity of the attenuated radiation that can be registered at the detector. Using the determined image acquisition parameters it is possible to estimate how high the image noise to be expected (and therefore the achievable image quality of the image exposure) will be with a given apparatus variable which, for example, pertains to a maximum achievable apparatus current and/or a set scan speed.

If the achievable image quality falls short of the desired image quality of the image exposure, an image region-dependent shortfall indicator is emitted; this means that an image region of the image exposure for which a shortfall is predicted is indicated by means of the shortfall indicator. The image region can be a single image region, but multiple image regions can also be addressed. For example, the corresponding shortfall indicator is emitted as a written data printout or as a hardcopy printout with overlaid regions of the shortfall. It is likewise possible to output the shortfall indicator as a screen display, a file or a written description.

Each quality parameter can be directly entered is an imported input. For example, this provides for the physician the possibility to manually input the desired quality parameter or parameters, which significantly increases and simplifies the operating comfort. The input advantageously ensues through a suitable importation device, for example via a keyboard of a computer or by means of a mouse pointer via a graphical user interface.

In a preferred embodiment, a planning image acquisition of the examination region is executed and the image acquisition parameters are determined using the planning image exposure.

The planning image acquisition is frequently a 2D image acquisition which entirely or partially acquires the examination region. For example, the presentation of the planning image exposure ensues on a corresponding presentation device, for example a computer monitor. Since no details have to be recognizable in the planning image exposure, the planning image exposure is normally acquired with a very, very poor image quality, and therefore with a significantly lower radiation exposure of the patient than the actual image exposure. The planning image exposure is appropriately executed in advance of the actual image exposure. It is particularly meaningful to execute the planning image acquisition and the image acquisition by means of the same image acquisition apparatus so that no movement of the patient to another bed is necessary between the individual acquisitions. The planning image acquisition is typically executed with a stationary x-ray source, similar to a conventional x-ray acquisition. The planning image exposure frequently shows the entire patient or a section of the examination region as an overview. Since the planning image exposure and the actual image exposure typically show the same image, a position of the image region in the planning image exposure significantly agrees with the position of the corresponding image region of the actual image exposure. A presentation of the planning image exposure by means of a suitable presentation device is frequently provided.

In an embodiment, the image region displayed by the shortfall indication is symbolically overlaid in the planning image exposure. In the scope of this embodiment variant, the image region displayed by the shortfall indicator is marked in the planning image exposure, for example via a semi-transparent color area. It is therefore recognizable in a simple manner in which image regions a reduced image quality is to be expected. A physician thereby recognizes at the first glance whether an image region of interest is affected by a reduced image quality. For example, in the framework of a planned, detailed image acquisition of the heart the image region of interest is the image region that depicts the heart. It is thus possible for a physician, in a simple and quick manner, to decide whether an adaptation of apparatus variables to increase the achievable image quality is necessary and reasonable.

In a preferred embodiment, the achievable image quality is overlaid in the planning image exposure symbolically and dependent on the image region. In this embodiment, an optical symbol is associated with the achievable image quality. For example, this symbol is overlaid in the corresponding image region overlaid in the planning image exposure. The symbol can also be understood as a number which, for example, indicates the percentile ratio of the achievable image quality to the desired image quality. For example, by the symbolic and image region-dependent overlay of the achievable image quality on the planning image exposure, it is made easier for a physician to make an estimation of the degree of a reduction of the desired image quality.

A color value is advantageously symbolically associated with the achievable image quality, and the color value is overlaid in the planning image exposure depending on the image region. In this embodiment the image region indicated by the shortfall indicator is marked, for example, by a semi-transparent color surface in the planning image exposure, wherein an achievable image quality is associated with the color associated with the area. For example, a dark red can be associated with a very low achievable image quality. The achievable image quality is color-coded, so to speak. Using such a color coding a physician (for example) can more easily recognize the achievable image quality that can be expected in each image region of the image exposure, and how significant the image quality reduction of the image exposure is.

A threshold for the achievable image quality is advantageously, predeterminably imported. The achievable image quality is compared with the threshold and, if the achievable image quality falls short of the threshold, the output of the image region-dependent shortfall indicator is suppressed. In particular an "accepted" achievable image quality is predetermined as the threshold. For example, such an "accepted" image quality is individually selected. Alternatively, the "accepted" image quality can be directly correlated with the desired image quality. Using this threshold, it is checked whether the actual achievable image quality lies within this acceptance level. If this is the case, the output of an image region-dependent shortfall indicator is suppressed. For example, this can be provided as a preventative measure in order to prevent an unnecessary adaptation of apparatus variables by the user.

In a preferred embodiment, if the achievable image quality falls short of the desired image quality, a modification suggestion to change one of the apparatus variables affecting the achievable image quality is additionally provided as an output. By affecting one or more apparatus variables it is in principle possible to affect and possibly to increase the achievable image quality. Parameters known as scan parameters for a computed tomography apparatus, for example the scan speed, the tube voltage and the scan time, are examples of apparatus variables that have an influence on the achievable image quality. In this embodiment, for example, are identifications of which apparatus variable should be changed for an improvement of the achievable image quality is made as on a modification suggestion. The modification suggestion can naturally also pertain to multiple apparatus variables. Furthermore, a modification value for the appertaining apparatus variable can also be proposed by means of the modification suggestion, for example. A user (for example a physician) can accept the modification suggestion or can ignore. For an acceptance of the modification suggestion, the physician will decide if the indicated image quality reduction pertains to the image region of interest. Otherwise it can also be reasonable to ignore the modification suggestion, for example for medical considerations.

A suggested modification range of the apparatus variable is advantageously output by means of the modification suggestion. The modification range encompasses modification values that lie between a minimal modification value and a maximum proposed modification value. For example, the specification of a modification range makes it possible for a physician to take medical considerations into account in the modification of the apparatus variable or variables. For example, the physician can decide to reduce one proposed apparatus variable (for example the scan speed) only slightly in order to not unnecessarily increase the applied dose, and can correspondingly alter a different suggested apparatus variable for achieving a comparable result. As a whole, by the output of such a modification suggestion it is easy for a user to estimate in an uncomplicated manner which apparatus variables can be varied and to what extent, in order to achieve an increase of the achievable image quality.

The modification range is advantageously symbolically presented and output as a slider element. The modification range here is visualized by means of the slider element and, for example, output as a screen overlay. A "slider element" means a longitudinal rectangular element, the ends which are respectively associated with a minimal and maximal proposed modification value of the modification range. The slider element can represent a purely graphical symbol, but an operable switching element of a graphical user interface can be advantageously marked and/or realized by means of the slider element. For example, it is possible to directly select a modification value in the modification range by means of a mouse pointer of the graphical user interface, which significantly increases the operating comfort.

An achievable image quality modified within the scope of changing the apparatus variable within the modification range is advantageously predicted and output. It is thus possible for a user to easily recognize what effect a modification of a proposed apparatus variable will likely have on the achievable image quality.

In a preferred embodiment, a color value is symbolically associated with the predicted achievable image quality and the color value is overlaid in the slider element dependent on the modification range. For example if, in the case of a modification of the proposed apparatus variable by the maximum modification value suggested by the modification range, an achievable image quality of 90% of the desired image quality is predicted, a corresponding color value (for example a light red) is associated with the end of the slider element associated with the maximum modification value of the modification range. By contrast, if an achievable image quality of 50% of the desired image quality is predicted for a modification of the proposed apparatus variable by the minimum modification value of the modification range, a different color value (for example violet) is associated with the end of the slider element associated with the minimal modification value of the modification range. What effects the modification of an apparatus parameter will presumably have on the achievable image quality is thus clear to a user at a first glance.

In a further embodiment, a modified apparatus variable is imported, a modified achievable image quality of the image exposure is deduced using the image acquisition parameters under consideration of the modified apparatus value, the modified achievable image quality is compared per image region with the desired image quality, and an image region-dependent shortfall indicator is output if the modified achievable image quality falls short of the desired image quality. The modified apparatus size is imported by a suitable importation device. For example, the importation device can be a graphical user interface. The input of the modified apparatus variable ensues by means of a mouse pointer operating the slider element, for example.

In a further embodiment of the invention, if the achievable image quality falls short of the desired image quality, an adaptation suggestion to adapt a quality parameter predetermining the desired image quality is additionally output based on an apparatus configuration, wherein an adaptation threshold is predetermined by the adaptation suggestion. The apparatus configuration pertains to the basic technical requirements of the image acquisition apparatus, for example the currently predetermined apparatus variables, such as the maximum achievable tube current. In this embodiment can be determined that an image acquisition can not be executed with the desired image quality under the circumstances, even by the modification of an apparatus variable, because the technical requirements for achieving this image quality are simply not present. In this embodiment it is therefore provided to output an adaptation suggestion for a reasonable adaptation of a quality parameter predetermining the desired image quality. A reduction of the desired image quality is in particular proposed by the adaptation suggestion. The adaptation threshold in particular pertains to a maximum proposed reduction of the desired image quality. In particular an image quality that essentially can be achieved by a corresponding modification of an apparatus variable is characterized by the adaptation threshold.

A modified quality parameter is advantageously imported, the modified quality parameter is compared with the adaptation threshold and, if the modified quality parameter exceeds the adaptation threshold, a modification warning is output. The modification warning is thus output when the technical requirements to execute the image acquisition with the adapted, desired image quality do not exist. In other words, this means that (for example) a physician is warned beforehand to further reduce the desired image quality. For this purpose, the modification warning can be overlaid in the presentation of the planning image, for example as a warning triangle. The modification warning can also be linked with an at least temporary blocking of a reduction of the desired image quality. An operating error by a user is thereby made more difficult overall.

A device for planning a medical imaging procedure according to the invention has an importation device, an image acquisition apparatus, a control device and an output device. With regard to an image acquisition that can be executed by means of an image acquisition apparatus, the importation device is configured to import a number of quality parameters—with regard to an image exposure that can be executed by means of the image acquisition apparatus—that associate a desired image quality with the image acquisition. For this purpose, the control device is configured to: determine a number of image acquisition parameters by means of the image acquisition apparatus; to determine an achievable image quality using the image acquisition parameters under consideration of one or each image acquisition parameter; to compare the achievable image quality per image region with the desired image quality; and to control the output device to output an image region-dependent shortfall indicator if the achievable image quality falls short of the desired image quality. The output device is configured to output the image region-dependent shortfall indicator.

The image acquisition apparatus is therefore advantageously configured to execute a planning image acquisition of the examination region.

A presentation device is advantageously provided that is configured to present the planning image exposure.

The advantages cited for the method are applicable to the device as well.

The importation device is, for example, a device to import external data, for example a CD-ROM drive or a suitable interface. Alternatively or additionally, the importation device is provided as (for example) a keyboard or as a graphical user interface of a computer via which (for example) a physician can advantageously directly input the quality parameters.

The image acquisition apparatus can be, for example, a C-arm x-ray system or a magnetic resonance system. Alternatively, the image acquisition apparatus can be a computed tomography apparatus.

For example, the control device can be in the form of a control module or a computer, or can be on a computer as software.

The presentation device is, for example, a monitor of a computer.

The output device can be, for example, a conventional printer that is suitable to output a hard copy printout. The output device can alternatively be a computer monitor. An output then ensues via the screen of the computer monitor.

DESCRIPTION OF THE PREFERRED EMBODIMENTS

Figure 1:
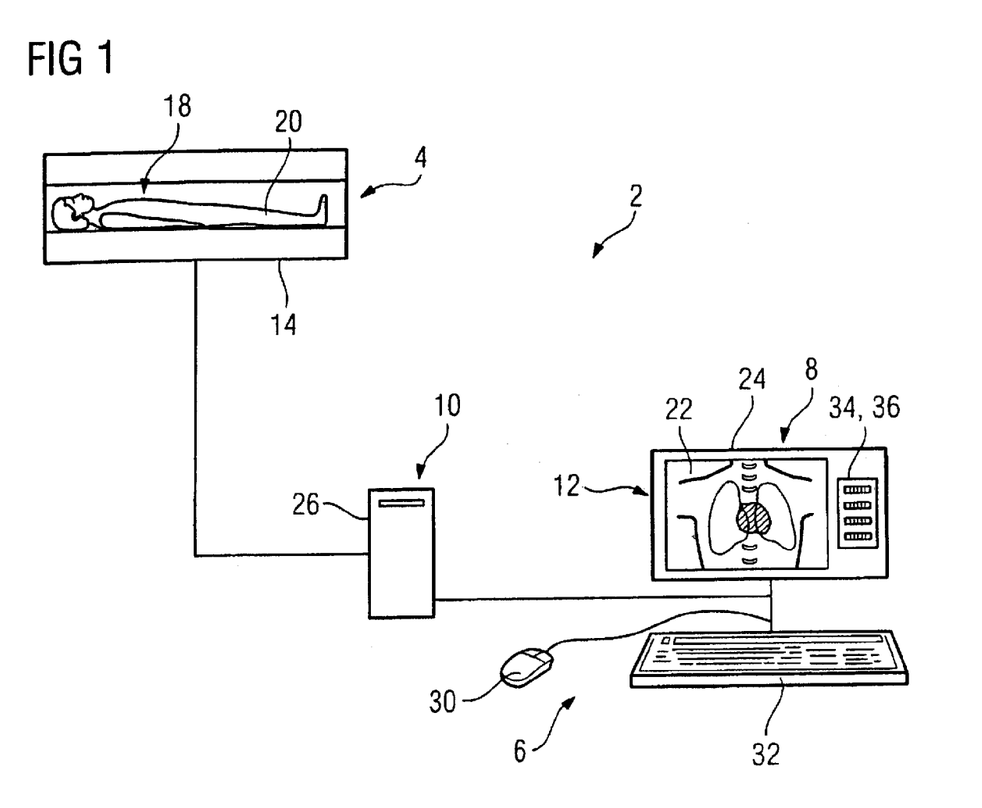
FIG. 1 schematically is a device for planning a medical imaging procedure according to the present invention.

The device shown in FIG. 1 for planning a medical imaging 2 comprises an image acquisition apparatus 4, an importation device 6, a presentation device 8, a control device 10 and a output device 12.

The image acquisition apparatus 4 here is executed as a computer tomography apparatus 14, called a CT apparatus for short in the following. The CT apparatus 14 is provided to execute a planning image exposure 22 to plan an image acquisition (not shown here) of an examination region 18 of a patient 20.

For this the CT apparatus 14 has an x-ray source and a detector (not visible), in particular in the form of a detector ring. The x-ray source and the detector are in particular arranged diametrically opposite one another.

The planning image exposure 22 is in particular a 2D image acquisition. The corresponding 2D image acquisition is executed with a stationary x-ray source, similar to a conventional x-ray acquisition. The patient 20 is typically radiographed from one direction by the x-rays emitted by the x-ray source while the patient 20 is slowly shifted through the x-ray field. The x-ray radiation passing through the patient 20 and attenuated by the passage strikes the detector, which generates detector signals that correspond to the intensity of the attenuated radiation. Due to locally different material properties of the tissue structures located in the beam path (for example organs, bones, etc.), the incident radiation is attenuated to a different degree in the passage through the body of the patient 20. The 2D planning image exposure 22 of the patient 20 can be determined and presented using the detector signals. The planning image exposure 22 here shows the examination region 18 in the manner of an overview, which examination region 18 is essentially provided as the chest of the patient 20. The executed planning image exposure 22 is presented by means of the presentation device 8 which here is provided as a computer monitor 24.

The control device 10 determines a number of image acquisition parameters using the planning image exposure 22, in particular using the corresponding detector signals which were imported via a corresponding interface. For this purpose, the control device 10 (which here is realized as a computer 26) has suitable determination software. The image acquisition parameters are values that describe the radiation attenuation property of the patient body along a radiography direction. The image acquisition parameters are determined using a comparison of the intensity of the attenuated radiation that can be registered at the detector with the intensity of the primary radiation emitted by the x-ray source. The locally different radiation attenuation relationships in the patient 20 thus can be described through the image acquisition parameters. Using the image acquisition parameters, the control device 10 derives an achievable image quality of the planned image exposure with the incorporation of one or more apparatus variables of the image acquisition apparatus 4. Here a tube current-time product is associated with the achievable image quality.

The achievable image quality is essentially defined by image noise. It is generally the case that, for a given setting of the apparatus variables, the image noise is higher the fewer x-ray quanta that can be registered by the x-ray detector of the CT 14. Thus, in a first approximation, that the greater the local radiation attenuation property of the patient body, the fewer x-ray quanta that can be registered at the detector, and so the higher the image noise and consequently the lower the achievable image quality of the image exposure. The tube voltage, the maximum achievable x-ray current, the scan speed, the scan time, the tube capacity, the feed speed of the patient bed of the CT, etc. are examples of relevant apparatus variables of the CT 14.

The quality parameters that associate a desired image quality with the image exposure are imported image acquisition the importation device 6. To import the desired image qualities, the importation device 6 includes a graphical user interface as well as a computer mouse 30 and a keyboard 32 of the computer 26. A number of input fields 34, 35 are realized on the graphical user interface. In one of the input fields 36 a physician can directly input the selected quality with the assistance of the mouse 30 and the keyboard 32. The quality parameter is input as a normalized current-time product in [mAs] units, which relates to an "average patient".

The control device 10 compares the achievable image quality of the image exposure with the desired image quality of the image exposure. If the control device 10 establishes in this comparison that the achievable image quality of the image exposure falls short of the desired image quality—thus if the desired image quality cannot be achieved with the given setting of the apparatus variables—the control device 10 controls the output device 12 to emit an image region-dependent shortfall indicator as an output.

The output device 12 here is formed the computer monitor 24 so that the output of the shortfall indicator occurs at the screen of the computer monitor 24.

Figure 2:
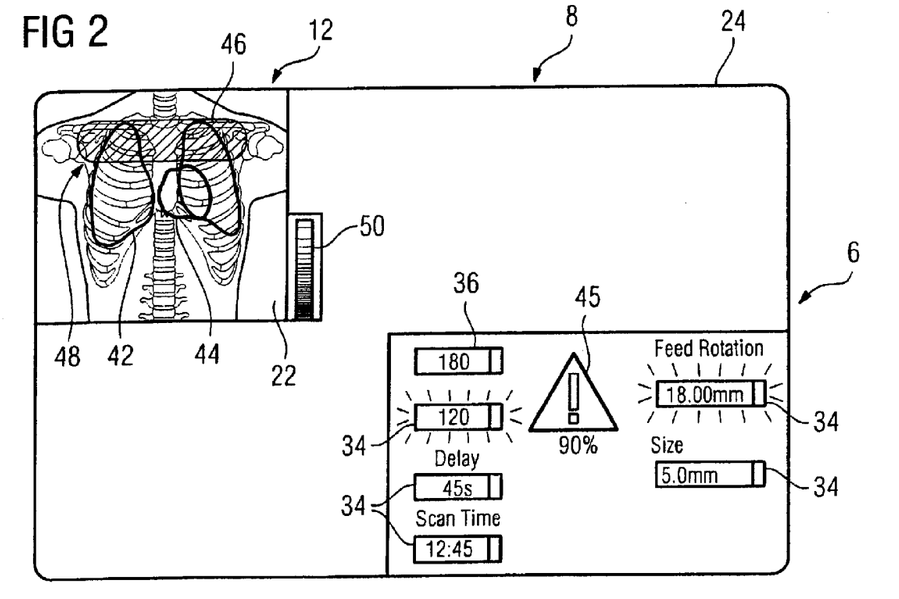
FIG. 2 shows a presentation device according to a first embodiment of the invention.

FIG. 2 shows a detailed view of the elements displayed by a presentation device 8 according to a first embodiment in the scope of a planning of medical imaging.

The planning image exposure 22 is shown in the left upper corner of the presentation device 8 shown here (which is provided as a computer monitor 24 as in FIG. 1). The planning image exposure 22 shows the examination region 18 of the patient 20 which here is essentially present as his chest. The lungs 42 and the heart 44 of the patient 20 are clearly recognizable.

The input fields 34, 36 and a warning triangle are displayed in the right lower corner of the presentation device 8. As described above, an input field 36 is provided to input the quality parameter which associates the desired image quality with the image exposure. The other input fields 34 contain a series of apparatus variables of the CT 14 according to FIG. 1, for example the tube voltage of the CT 14, the scan time, a slice thickness, a feed speed of a patient bed of the CT 14 and a "delay" time.

The achievable image quality falling short of the desired image quality was established by the control device 10 according to FIG. 1 in the scope of the method described in FIG. 1.

Depending on the established shortfall of the desired image quality by the achievable image quality, the achievable image quality is compared with a threshold by the control device 10 according to FIG. 1. The corresponding threshold is a measure for the "accepted" achievable image quality. Here a fixed value of 90% of the desired image quality was predetermined as a threshold. Since the achievable image quality falls short of this threshold of the "accepted" image quality, meaning that the achievable image quality is less than the image quality predetermined by the threshold, the output of the image region-dependent shortfall indicator is not suppressed.

The control device 10 correspondingly controls the output of an image region-dependent shortfall indicator. The corresponding output of the shortfall indicator occurs via the screen of the computer monitor 24.

The image region 46 indicated by the shortfall indicator is hereby symbolically represented by means of an overlay 48 in the form of a semi-transparent color area in the planning image exposure 22.

Via the overlay 48, in which image region 46 a reduced image quality is to be expected in the scope of the planned image exposure is apparent to the physician in a simple manner.

The image quality achievable in the image region 46 is symbolically indicated by means of the color area of the overlay 48. For this purpose, a color value is associated with the achievable image quality; the achievable image quality is color-coded, so to speak. A percentile value can be associated with the achievable image quality, this percentile value specifying what percentage of the desired image quality will be achieved by the achievable image quality. A light grey is hereby associated with a high percentage while the corresponding grey tone becomes darker with decreasing achievable image quality. The color area of the overlay 48 thus overall shows a color curve from light grey to dark grey. A color scale 50 is additionally overlaid in the presentation to the right of the planning image exposure 22, from which color scale 50 it is apparent which grey tone is associated with which percentile portion of the desired image quality.

For example, using such a color coding a physician can recognize at the first glance how significant the image quality reduction to be expected is within the image region 46. Overall, the overlay 48 enables the physician to quickly detect whether an image region of interest is affected by the reduced image quality. The planned image exposure here is provided in the framework of a detailed image exposure of the heart 44, such that the image region that depicts the heart 44 is what is the image region of interest.

In addition to the overlay 48, by means of which the image quality achievable in the image region 46 is displayed with color coding, the control device 10 controls the output of a warning triangle 45 on the screen of the computer monitor 24. The warning triangle 45 shows the value of the "worst" achievable image quality that is predicted within the image region 46. A physician thereby reviews at a glance how high an expected reduction of the image quality is in the worst case.

By influencing one or more apparatus variables of the CT 14 according to FIG. 1, it is possible in principle to increase the achievable image quality. Therefore the output of a modification suggestion to modify an apparatus variable is provided dependent on the established short fall of the desired image quality by the achievable image quality. In this embodiment, by means of the modification suggestion in particular a suggestion is output as to which apparatus variable can reasonably be changed to improve the achievable image quality. For this purpose, the input fields 34 that contain the corresponding apparatus variables proposed for modification are marked with an obvious color background.

With the output of the modification suggestion, it is simpler for a user (in particular a physician) to estimate which apparatus variable(s) should reasonably be altered to increase the achievable image quality.

Figure 3:
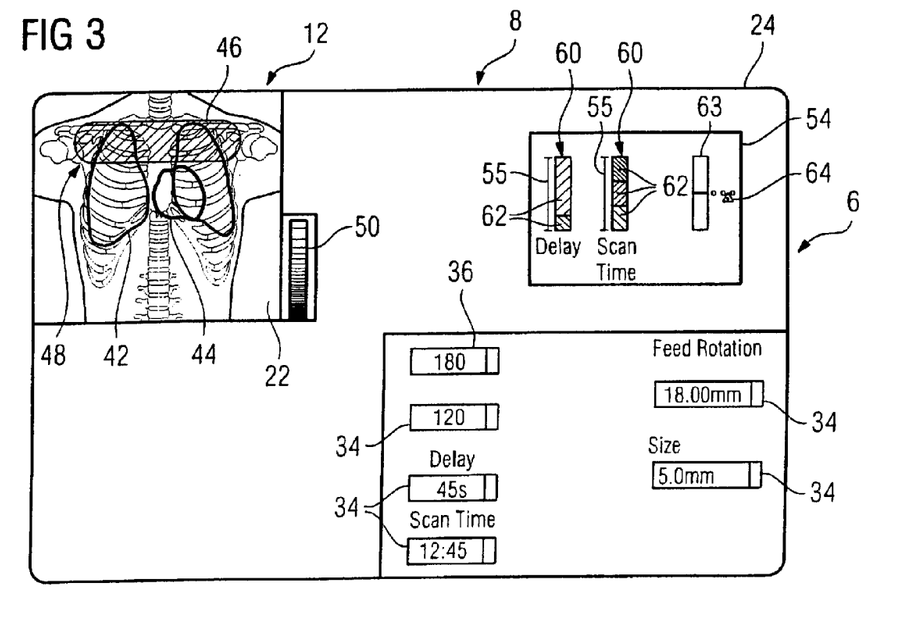
FIG. 3 shows a presentation device according to a second embodiment of the invention.

FIG. 3 shows a view of the elements shown by a presentation device 8 according to a second embodiment variant in the scope of planning of a medical imaging.

As in FIG. 2, the planning image exposure 22 is presented in the left upper corner of the presentation device 8 shown here, and the image region 46 indicated by the shortfall indicator is likewise marked by means of the overlay 48 in the form of a semi-transparent color surface in the planning image exposure 22. A row of input fields 34, 36 is likewise displayed in the right lower corner of the presentation device 8.

The overlay of a modification window 54 is provided to output the modification suggestion. In addition to the suggestion of which apparatus variable can reasonably be changed to improve the achievable image quality, a suggested modification value for the apparatus variable (in particular in the form of a modification range 55) comes from the modification suggestion of this embodiment. In the shown example the modification of two apparatus variables is suggested. The modification range 55 of the appertaining apparatus variable is respectively visualized by a slider element 60 and output as a screen overlay. The two ends of each slider element 60 are associated with a minimum or, respectively, a maximum proposed modification value.

Here the slider elements 60 respectively mark an operable switching element of the graphical user interface of the importation device 6. For example, a physician can simply select the desired modification value of the corresponding apparatus variable using the slider element 60 by means of a mouse pointer, which significantly increases the operator comfort.

As can be seen from the depiction, the slider elements 60 exhibit a series of color regions 62. The color regions 62 mark sub-ranges within the proposed modification range 55 of the appertaining apparatus variable. A predicted, modified achievable image quality thereby is apparent from the color marking of the partial ranges 62. For this purpose, color values are respectively symbolically associated with the predicted achievable image quality, and the corresponding color value is overlaid in the slider element 60 depending on the modification range. The effects that the modification of an apparatus parameter predictably have on the achievable image quality are thus apparent to a user (for example a physician) at first glance.

Through the graphical user interface of the importation device 6, it is possible for a user to select the desired modification value of the corresponding apparatus variable using the slider element 60 and to execute the selection. The confirmed, modified apparatus variable is imported by means of the importation device 6. Taking the modified apparatus variable into account, the control device derives a modified achievable image quality of the planned image exposure.

In contrast to FIG. 2, the output of an adaptation suggestion for adaptation of the quality parameter predetermining the desired image quality is additionally provided. The adaptation suggestion here is displayed in the form of an operable switching element 63 of the graphical user interface within the modification window 54. In particular, a reduction of the desired image quality is proposed by means of the adaptation suggestion. It is taken into account that an image exposure in particular cannot be executed under the circumstances with the given desired image quality, even by changing an apparatus variable, since the technical requirements for this are not present. The adaptation suggestion contains an adaptation threshold which in particular marks a reduced desired image quality that can essentially be achieved via a corresponding modification of an apparatus variable.

The adaptation threshold is correlated with a modification warning which appears overlaid in the screen of the computer monitor 24 as a warning symbol 64. For example, with the modification earning a physician is warned to further reduce the desired image quality when the technical requirements to execute the image exposure are essentially present, in particular with the reduced, desired image quality. Moreover, here a blocking of an additional reduction of the desired image quality is accompanied by the modification warning. An operating error by a user is thereby made more difficult overall. The blocking can be removed as necessary by the user by a corresponding operation of the warning symbol 64 by means of a mouse pointer. If the block is removed, for example, an overlay of a warning notice can be provided which informs the user that an additional reduction of the currently desired image quality could result in a worse image quality than the image quality that is currently achievable.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for planning a medical imaging procedure, comprising the steps of:
   importing a plurality of quality parameters into a controller that controls a medical image acquisition apparatus configured to obtain a medical image exposure of a patient, comprising a plurality of regions of the patient, by irradiating said plurality of regions of the patient with radiation, said plurality of quality parameters respectively associated a desired image quality with said plurality of regions;
   in said controller, determining a plurality of image acquisition parameters that respectively characterize local radiation attenuation properties of said plurality of regions;
   automatically determining an achievable image quality of said medical image exposure, using said image acquisition parameters and an apparatus variable of said medical image apparatus that influences the image quality of said medical image exposure;
   in said controller, automatically comparing, for each of said regions, the achievable image quality with the desired image quality, to obtain a comparison result; and
   if said comparison result indicates that said achievable image quality falls short of said desired image quality, emitting a shortfall indicator from said controller that also identifies in which region or regions, among said plurality of regions, said achievable image quality falls short of said desired image quality.

2. A method as claimed in claim 1 comprising entering each image quality parameter into said controller directly through an input unit connected to said controller.

3. A method as claimed in claim 1 comprising:
   acquiring a planning image exposure of said patient using said medical image acquisition apparatus; and
   from said planning image exposure, automatically determining, in a processor, said plurality of image acquisition parameters, and supplying said image acquisition parameters to said controller.

4. A method as claimed in claim 3 comprising displaying said planning image, and emitting said shortfall indicator as a symbolic overlay in the planning exposure.

5. A method as claimed in claim 4 comprising symbolically overlaying said shortfall indicator in said planning exposure on any of said regions for which said achievable image quality falls short of said desired image quality.

6. A method as claimed in claim 5 comprising automatically associating a symbolic color value with said achievable image quality, and overlaying said shortfall indicator with said color value in said planning image exposure.

7. A method as claimed in claim 1 wherein the step of comparing said achievable image quality with said desired image quality comprises entering a threshold for said achievable image quality into said controller and comparing said achievable image quality with said threshold, and suppressing emission of said shortfall indicator as long as said achievable image quality exceeds said threshold.

8. A method as claimed in claim 1 comprising, in said controller, if said achievable image quality falls short of said desired image quality, automatically generating a modification suggestion for changing said apparatus variable, to improve said achievable image quality.

9. A method as claimed in claim 8 comprising generating a suggested range for said apparatus variable as said modification suggestion.

10. A method as claimed in claim 9 comprising, at a display connected to said controller, displaying said modification suggestion as a graphical slider representing said range for said apparatus variable.

11. A method as claimed in claim 9 comprising, at a display connected to said controller, displaying said range of said apparatus variable using a graphical symbol allowing selection of a value for said apparatus variable within said modification range and, in said controller, upon selection of a value for said apparatus variable in said range, predicting the achievable image quality that will result therefrom and displaying the predicted image quality at said display.

12. A method as claimed in claim 11 comprising at said display, symbolically associating a color value with the predicted achievable image quality, and overlaying said color value on said graphical symbol dependent on the range.

13. A method as claimed in claim 1 comprising:
   upon emission of said shortfall indicator, allowing entry of a modified value for said apparatus variable into said controller;
   in said controller, automatically determining a modified achievable image quality of said image exposure using the modified apparatus variable and said image acquisition parameters and automatically comparing said modified achievable image quality, for each region in said plurality of regions, with said desired image quality; and
   emitting said shortfall indicator if said modified achievable image quality still falls short of said desired image quality as a result of said comparison.

14. A method as claimed in claim 1 comprising, upon emission of said shortfall indicator, automatically calculating an adaptation suggestion to adapt at least one of said quality parameters dependent on said image acquisition parameters and said apparatus variable, and displaying said adaptation suggestion at a display connected to said controller.

15. A method as claimed in claim 14 comprising generating said adaptation suggestion as a threshold for said at least one of said quality parameters.

16. A method as claimed in claim 15 comprising:
   entering a modified value of said at least one of said quality parameters into said controller;
   in said controller, comparing said modified value with said adaptation threshold; and
   if said modified value exceeds said adaptation threshold, emitting a modification warning as a humanly perceptible output from said controller.

17. An apparatus for planning a medical imaging procedure, comprising:
   a medical imaging apparatus operated by a controller;
   said controller being configured to said control medical image acquisition apparatus to obtain a medical image exposure of a patient, comprising a plurality of regions of the patient, by irradiating said plurality of regions of the patient with radiation, according to a plurality of quality parameters respectively associated a desired image quality with said plurality of regions;

said controller being configured to determine a plurality of image acquisition parameters that respectively characterize local radiation attenuation properties of said plurality of regions;

said controller being further configured to automatically determine an achievable image quality of said medical image exposure, using said image acquisition parameters and an apparatus variable of said medical image apparatus that influences the image quality of said medical image exposure;

said controller being further configured to automatically compare, for each of said regions, the achievable image quality with the desired image quality, to obtain a comparison result, and if said comparison result indicates that said achievable image quality falls short of said desired image quality, to emit a shortfall indicator from said controller that also identifies in which region or regions, among said plurality of regions, said achievable image quality falls short of said desired image quality.

18. An apparatus as claimed in claim 17 comprising an input unit connected to said controller allowing entry of each image quality parameter into said controller directly.

19. An apparatus as claimed in claim 17:
wherein said controller is configured to operate said medical image acquisition apparatus to acquire a planning image exposure of said patient; and
said controller being configured, from said planning image exposure, to automatically determine said plurality of image acquisition parameters.

20. An apparatus as claimed in claim 17 comprising a display, and wherein said controller is configured to display said planning image, and to emit said shortfall indicator as a symbolic overlay in the planning exposure.

21. An apparatus as claimed in claim 20 comprising wherein said controller is configured to symbolically overlay said shortfall indicator in said planning exposure on any of said regions for which said achievable image quality falls short of said desired image quality.

22. An apparatus as claimed in claim 21 wherein said controller is configured to automatically associate a symbolic color value with said achievable image quality, and to overlay said shortfall indicator with said color value in said planning image exposure.

23. An apparatus as claimed in claim 17 wherein said controller is configured to compare said achievable image quality with said desired image quality using a threshold for said achievable image quality, by comparing said achievable image quality with said threshold, and suppressing emission of said shortfall indicator as long as said achievable image quality exceeds said threshold.

24. An apparatus as claimed in claim 17 wherein said controller is configured, if said achievable image quality falls short of said desired image quality, to automatically generate a modification suggestion for changing said apparatus variable, to improve said achievable image quality.

25. An apparatus as claimed in claim 24 wherein said controller is configured to generate a suggested range for said apparatus variable as said modification suggestion.

26. An apparatus as claimed in claim 25 comprising a display connected to said controller, and wherein said controller is configured to display said modification suggestion as a graphical slider representing said range for said apparatus variable.

27. An apparatus as claimed in claim 25 comprising a display connected to said controller, and wherein said controller is configured to display said range of said apparatus variable using a graphical symbol allowing selection of a value for said apparatus variable within said modification range and, upon selection of a value for said apparatus variable in said range, to predict the achievable image quality that will result therefrom and displaying the predicted image quality at said display.

28. An apparatus as claimed in claim 27 wherein said control is configured to symbolically associate a color value with the predicted achievable image quality at said display, and to overlay said color value on said graphical symbol dependent on the range.

29. An apparatus as claimed in claim 17 wherein said controller is further configured to:
upon emission of said shortfall indicator, allow entry of a modified value for said apparatus variable into said controller;
automatically determine a modified achievable image quality of said image exposure using the modified apparatus variable and said image acquisition parameters and to automatically compare said modified achievable image quality, for each region in said plurality of regions, with said desired image quality; and
emit said shortfall indicator if said modified achievable image quality still falls short of said desired image quality as a result of said comparison.

30. An apparatus as claimed in claim 17 comprising a display connected to said controller, and wherein said controller is configured, upon emission of said shortfall indicator, to automatically calculate an adaptation suggestion to adapt at least one of said quality parameters dependent on said image acquisition parameters and said apparatus variable, and to display said adaptation suggestion at said display connected to said controller.

31. An apparatus as claimed in claim 30 wherein said controller is configured to generate said adaptation suggestion as a threshold for said at least one of said quality parameters.

32. An apparatus as claimed in claim 31 wherein said controller is configured to:
receive a modified value of said at least one of said quality parameters;
compare said modified value with said adaptation threshold; and
if said modified value exceeds said adaptation threshold, emit a modification warning as a humanly perceptible output from said controller.

* * * * *